US006989904B2

(12) United States Patent
Moersen et al.

(10) Patent No.: US 6,989,904 B2
(45) Date of Patent: Jan. 24, 2006

(54) METHOD OF DETERMINING LOCAL STRUCTURES IN OPTICAL CRYSTALS

(75) Inventors: Ewald Moersen, Mainz (DE); Axel Engel, Ingelheim (DE); Christian Lemke, Jena (DE); Guenter Grabosch, Mainz (DE)

(73) Assignee: Schott AG, Mainz (DE)

( * ) Notice: Subject to any disclaimer, the term of this patent is extended or adjusted under 35 U.S.C. 154(b) by 369 days.

(21) Appl. No.: 10/464,402

(22) Filed: Jun. 18, 2003

(65) Prior Publication Data

US 2004/0021803 A1 Feb. 5, 2004

(30) Foreign Application Priority Data

Jun. 19, 2002 (DE) ................................ 102 27 345

(51) Int. Cl.
*G01B 9/02* (2006.01)
*G01N 21/00* (2006.01)
*G01J 4/00* (2006.01)

(52) U.S. Cl. .................... 356/495; 356/73; 356/369
(58) Field of Classification Search .................. 356/73, 356/129, 364–370, 237.1, 239.1, 239.2, 30, 356/32, 491–495, 518
See application file for complete search history.

(56) References Cited

U.S. PATENT DOCUMENTS

| 3,468,610 A | * | 9/1969 | Muffoletto ................... 356/129 |
| 5,086,352 A | | 2/1992 | Yamagata et al. |
| 5,364,433 A | | 11/1994 | Nishimura et al. |
| 5,648,850 A | * | 7/1997 | Basler et al. ................ 356/369 |
| 5,764,363 A | * | 6/1998 | Ooki et al. ................... 356/364 |
| 5,790,315 A | | 8/1998 | Fujinoki et al. |
| 5,875,029 A | * | 2/1999 | Jann et al. ................... 356/491 |
| 6,891,980 B2 | * | 5/2005 | Gerhard et al. ............. 382/321 |
| 2001/0030798 A1 | | 10/2001 | Fujinoki et al. |

FOREIGN PATENT DOCUMENTS

DE  100 05 051 A1  5/2001
DE  101 11 450 A1  9/2002

OTHER PUBLICATIONS

A. Engel et al: "Present and Future Industrial Metrology . . . " Optical Metrology Roadmap for the Semiconductor, Optical and Data Storage Industries II, San Diego, CA, USA, Aug. 2-3, 2001, 4449, pp. 1-6.

Nishida et al: "Developments of a Two-Dimensional Birefringence . . . " Review of Scientific Instruments, May 2001, AIP, USA, 72 (5), pp. 2387-2391.

\* cited by examiner

*Primary Examiner*—Hwa (Andrew) Lee
*Assistant Examiner*—Patrick Connolly
(74) *Attorney, Agent, or Firm*—Michael J. Striker

(57) ABSTRACT

The method for determining local structures in optical materials, especially crystals, includes observing schlieren visually in a material to be tested with divergent white light in a first step; measuring birefringence of polarized laser light in the material to determine local defects and structure faults in the material with a spatial resolution of 0.5 mm or better in a second step if the material is judged to be suitable in the first step and then interferometrically measuring the material to determine the faults in the material by interferometry in a third step if the material is judged to be suitable in the first and second steps. This method can be part of a method for making optical components, especially for microlithography.

19 Claims, 3 Drawing Sheets

METHOD OF DETERMINING LOCAL STRUCTURES IN OPTICAL CRYSTALS

BACKGROUND OF THE INVENTION

The present invention relates to a method of determining local structures in optical materials, especially crystals, and, more particularly, to a method of determining local structures in materials for microlithography, e.g. from calcium fluoride, and to the optical elements obtained from them.

For optical applications both in glasses and also in crystals the optical properties are specified in great detail besides the form or shape of the particular product. In addition these optical properties in glasses and crystals include properties, such as transmission, homogeneity of the index of refraction and interior quality, which can be damaged by bubbles and inclusions or schlieren. In crystals the interior quality is described by the so-called real structures, including point defects, dislocations and grain boundaries, especially small-angle grain boundaries. These defects or imperfections are frequently very much spatially located, in contrast to similar defects in glass. However they have a very strong influence on the physical effects connected with them, such as absorption properties, homogeneity of the index of refraction and double refraction or birefringence.

The use of crystals for optical components is continuously increasing especially because of the increasing use of wavelengths, which are outside the visible range and which are not transmitted through glass. There is thus an increasing demand for monocrystalline materials made from alkali metal fluorides and alkaline earth fluorides ($CaF_2$, $BaF_2$, $SrF_2$ and so forth) for UV applications, such as UV lithography or lenses and windows for irradiating units and imaging units. The same is true for crystals in the infrared spectral region, which are required for many optical elements.

Particularly calcium fluoride single crystals ($CaF_2$) are required as the starting material for optical components in DUV photolithography (DUV=deep UV) at wavelengths around or under 200 nm, especially at wavelengths of 248 nm, 193 nm and 157 nm, of the Excimer laser. These optical components are usually lenses, prisms and plates in the so-called steppers or excimer lasers. They serve particularly to optically form the fine structured integrated circuits on photolacquer coated semiconductor disks and/or with the masks used in photolithography.

The semiconductor disks are always increasing in size. Currently the semiconductor disks are already 250 mm. On the other hand, the semiconductor structures are always getting. Structure widths of 250 nm are already standard. Thus the optical components and/or the materials for them must have the required quality over their entire volume (for example round disks with about 250 nm diameter and about 50 mm thickness), also, on a small-scale.

Thus $CaF_2$ crystals for applications in projection optics for the UV and DUV range must be free of coarse or gross defects, such as grain boundaries. For optical applications only crystals, which are single crystals over their entire volume, can be considered. A single crystal has primarily a desired orientation determined by a certain application, e.g. a crystallographic orientation <111>, <100> and <110>. Whether this single crystal is usable primarily for the desired optical purpose and for which application is determined by the local structures, such as disturbances and crystal defects, in the single crystalline region.

Single crystals are characterized by a long-range periodic crystal structure in bulk and thus a priori have a higher uniformity or homogeneity of physical properties. However since all parameters, especially heat flow, are not completely under control during the making of a single crystal in the crystal growth apparatus, the so-called real structure with standard defects forms during crystallization. Thus, for example, regions with birefringence and blocks with crystal orientations that are slightly different from each other arise. The orientation variations are within an angular range of about 1° to 5°. These local real structures limit the quality of the crystal in practice. Thus they may not exceed certain limiting values when such a crystal is used in a highly accurate optical system, such as a projection optic system for a stepper, which operates at 248 nm, 193 nm or 157 nm.

The local structures occurring in the above-described single crystals for optical applications are, above all, accumulations of defect locations, dislocations, glide planes and small-angle grain boundaries. Dislocations are statistically distributed defects and glide planes or glide strips are planar defects. Small-angle grain boundaries are boundary surfaces, which separate crystal regions with comparatively slight orientation differences (less than 10 degrees). Impurities frequently collect at small-angle grain boundaries, which are for example CaO deposits in the case of $CaF_2$.

Small-scale structures only play a very subordinate role in the characterization of optical glasses. The quality of optical glasses is determined essentially by long-range inhomogeneities. Accordingly only gross or large-scale defects or faults are measured. The measurements have only a comparatively low spatial resolution.

When measurement methods commonly used for glass are transferred to or used for crystals, typical crystal defects are missed or not determined. As a result of that experiments that measure the quality of the starting crystals often produce good results. The crystals are judged acceptable for a wide range of applications. However often when optical components are built from the crystals, they do not meet the required specifications. Since small-scale defects arise also in glasses and other optical—also non-crystalline—materials, which interfere in optical systems with comparatively higher resolution, they may not be detected by the above-described methods.

These local small-scale defects in the structure of a "single-crystal" are thus decisive for the use of a crystal, for example, in projection optics for microlithography in the UV region and in the far UV region, which means wavelengths less than 200 nm.

SUMMARY OF THE INVENTION

It is an object of the present invention to provide a method for determining essentially all the above-described real structures or local structures in materials, which influence the quality of these materials for optical applications, prior to the further processing of these optical raw materials to form an optical component.

According to the invention the method for determining or detecting local structures in optical materials, especially crystals, comprises the steps of:

a) observing schlieren visually in a material to be tested with divergent white light;

b) measuring birefringence of polarized laser light in the material to be tested so as to determine local defects and structure faults in the material with a spatial resolution of at least 0.5 mm; and c) interferometrically measuring the material to be tested so as to determine the faults in the material to be tested by interferometry.

The method according to the invention is thus based on a combination of several determinations. In particularly a visual determination of the schlieren by white light, which provides a first rough guide or coarse view and is a subjective measurement, is performed. This observation is performed with an arbitrary, especially low, spatial resolution. It is limited only by the visual acuity of the observer. This first rough guide sorts out those materials, whose quality does not achieve the required value in any case. These unacceptable materials need not be tested in the second and third steps of the method, which are performed with higher local resolution.

In the second step, which is based on polarization methods, the samples of the optical material are subjected to a laser measurement. Here the birefringence of the transmitted light is measured with the aid of the polarization, however now with a spatial resolution of generally at least 0.5 mm, preferably higher than 0.3 mm ("higher" means smaller than 0.3 mm), especially preferably higher than 0.2 mm, and even more preferably higher than 0.1 mm. The laser beam passes through a sample of material to be tested and the transmitted laser beam is detected and/or determined on a grid of pixels in a point-wise manner. The spacing of the scanned pixels and the width of the laser beam determine the spatial resolution of the local birefringence. Because of those features small local structures are discovered which could not be detected with the currently used methods.

Because of these methods it is possible now to determine not only the maximum and the average values for the faults or defects in a material and/or crystal sample or disk, but to determine the exact location of these faults or defects. Materials and/or crystals, which have poor quality at individual locations, could already be sorted out and if necessary supplied for alternative uses, for which smaller high quality disks were required. These faults especially are local defects and dislocations in the bulk material or crystal structures, which interfere with the optical uniformity of the material.

The limiting value for the birefringence should be as small as possible and preferably should not exceed 1.0 nm/cm and/or 0.5 nm/cm, preferably 0.4 nm/cm and especially preferably should not exceed 0.3 nm/cm.

Finally the material disk is subjected to an interferometric measurement, in which the test sample is similarly scanned. Here a measurement with high local resolution is performed. In interferometry the entire sample is simultaneously irradiated and the image contains transit time or phase difference information. The brightness values of the digital image received in this manner are evaluated in a point-wise manner and the locally resolved measured values are obtained. This sort of method is also described in the unpublished application DE-A 101 11 450 of the same inventors as the present invention.

Thus local small-scale structures are detected and evaluated with high accuracy and high local resolution interferometrically and optically under mechanical stress. The defect or fault detection takes place in starting material for optical components, which means in preferred embodiments in crystals, such as $CaF_2$ crystals, or in the disks made from the materials to be tested.

The methods according to the invention are suitable not only for crystals, but generally for the characterization and/or testing of optical materials. These optical materials include glass, quartz, quartz glass, optical plastic materials and crystals, especially halogen crystals and oxide crystals. The fluoride and halide crystals are especially preferred among the halide crystals. Alkali metal halide or oxide crystals or alkaline earth halide or oxide crystals, especially calcium sodium, lithium, strontium, calcium, magnesium or barium halide or oxide crystals, are preferred.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which.

DETAILED DESCRIPTION OF THE INVENTION

To characterize optical materials it is standard to measure the stress birefringence in materials with the help of a polariscope or polarimeter. These measurements of course facilitate qualitative evaluation of the material and/or crystal, however only a gross quantitative analysis of the crystals and/or material. Furthermore these measurements do not permit a full-surface and exact quantitative analysis. However with materials, such as $CaF_2$ crystals, which are provided for use in projection optics for photolithography, that is exactly what is required based on local structures of these materials.

In preliminary experiments it was established that the local structures have a higher birefringence by about a factor of ten or even higher than fault or defect free material and/or crystal regions. These strong local changes of the properties, which cause a reduction in the contrast of these systems, are especially critical for photolithography applications. Furthermore a portion of the radiated energy is usually absorbed in those local structures, which leads to a local heating of the optical lens, prism, etc. and thus also to local changes of the index of refraction and the image resolution or definition.

Figure 1:
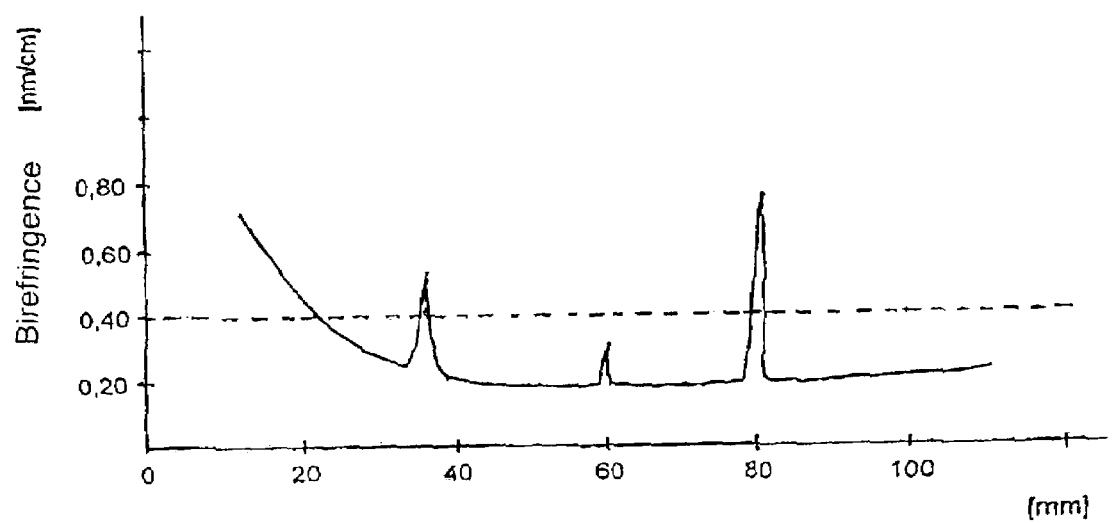
FIG. 1 is a graphical illustration showing the dependence of the stress birefringence of a calcium fluoride crystal disk on the location in the crystal disk.

FIG. 1 shows, for example, the dependence of the birefringence of a $CaF_2$ disk on a position of a beam scanned over the disk. The action of longer-range inhomogeneities, such as changes in the chemical composition, reflect themselves in the comparatively weak curvature of the general form of the curve. Peaks and/or teeth on this curve indicate the local structures and crystal faults. These short-range inhomogeneities are detected with the local resolution achieved in the methods according to the invention. In individual cases the birefringence can largely exceed there the given limiting value of, for example, 40 nm/cm (dashed line).

Crystals for microlithography should have no birefringence locally in regions less than 1 mm in diameter, preferably in regions less than 0.5 mm. Generally the birefringence should be only slight and preferably less than 5 nm/cm, especially less than 1 nm/cm. In other words, the difference between two adjacent measuring points should preferably be less than 5 nm/cm, especially less than 1 nm/cm. The phase shift of the schlieren in the crystals should be under 5 nm, preferably under 1 nm. The values of the local structures should be at most about a factor of 5 greater than the RMS average values, preferably at most about a factor of 3.

Materials, such as $CaF_2$-crystals, could be subjected to a visual schlieren control according to specification MIL G174-B analogous to optical glass. Thus especially the defects designated as small-angle grain boundaries are produced. These "schlieren" are frequently described as the so-called C-schlieren and D-schlieren according to MIL G174-B in optical glasses. Only schlieren-free and/or schlieren-poor crystals (Degreee A 0, schlieren-free, maximum degree B) are suitable for microlithography applications. The measurements of the schlieren must have a spatial resolution of better than 0.2 mm for sufficient detection.

In order to prepare an especially pure and possibly structure-free material for microlithography, not only the gross inhomogeneities, but also the small microstructures must be avoided. These microstructures occur in small limited spaces and for example are formed by glide planes or also by small-angle grain boundaries, at which impurities are deposited and thus appear also as schlieren. In order to detect these defects and microstructures with higher precision a series of measurements are performed one after the other.

In a first step the material disk cut from the obtain crystal is subjected to a visual schlieren control according to specification MIL G174-B with white light. Only schlieren-free and/or schlieren-poor materials (degree A0, maximum degree B according to MIL G174-B) are measured further. Materials and/or material disks that do not fulfill these requirements can be subjected to an additional tempering step and subsequently tested once again.

In this way a first rough guide or coarse observation occurs, which indeed is only subjective, and detects only comparatively large area defects. However it is useful to sort out unsuitable materials, which do not fulfill the minimum requirements.

The schlieren measurement can occur automatically so that the shadow image of the sample is received on a projection screen by an electronic imaging device, such as a digital CCD camera. The image of the sample is subjected to an image processing, which determines the contrast of the structures in the image. The contrast established in the image is compared with patterns. The comparison results are then used to evaluate the sample. This sort of process is described in detail in the unpublished application DE-A 101 11 450 of the same inventors as the present invention.

In the foregoing manner a sample is irradiated with divergent light from a light source and a real shadow image of the sample is produced on a projection screen. The shadow image of the sample on the projection screen is captured by an electronic image-taking device, for example a CCD camera. The shadow image of the sample received by the electronic-image taking device is then subjected to an image processing, which determines the image contrast of the schlieren. Then the image contrast for the sample is compared with the image contrast in a shadow image of a schlieren pattern on a synthetic schlieren plate. The schlieren in the sample of the optical material is then evaluated with the aid of the comparison results. The comparison pattern of the synthetic schlieren plate is usually measured interferometrically. The interferometric measurement calibrates the image contrast detected on the sample. Preferably the synthetic schlieren plate comprises the same material, as the sample of the optical material to be evaluated. However it is also possible to use a synthetic schlieren plate made from another material than the optical material of the test sample being evaluated. This latter schlieren plate is calibrated with a synthetic schlieren plate made from the optical material to be evaluated interferometrically. The synthetic schlieren plate preferably has artificial schlieren with a positive phase shift in steps of about 5 nm until about 50 nm and widths of about 0.1 nm to about 0.5 nm with a wavelength of 550 nm. Principally it is preferred to tilt and to rotate the sample relative to the optical axis of the measurement structure for the shadow methods in a number of directions.

In this step the sample can be also irradiated with a light beam and the image on the screen, on which the light falls after passing the sample, can be received by a CCD camera as a digital image. The received digital image may be inverted in its brightness values on a point-by-point basis (pixel for pixel).

If the disks evaluated grossly in the first step are found to be sufficient or satisfactory, they are subjected to a laser measurement with a higher spatial resolution in a second step.

The second step is based on polarization methods. Also the birefringence is determined here with the aid of polarization of light passing through the sample. In this process the local birefringence is measured in small regions over the entire material sample disk with grid spacing of at most 0.5 to 0.3 mm, preferably at most 0.2 mm and still better at most 0.1 mm, with a monochromatic laser beam. Since the laser beam has a diameter of for example 1 mm, the individual measured points overlap accordingly.

In this way in the second step also small local structures are detected very exactly and determined. Because of that it is now possible to find not only an upper limiting value and average value of the schlieren in a material disk, but these values can also be accurately located. In this way it is possible to sort out optical materials, such as crystals, which have locally poor values at individual locations. Alternatively the material bodies and/or the crystals can be divided so that only their good regions are used to make optical components.

The limiting value for local birefringence can, for example, be 0.5 nm/cm or 0.4 nm/cm or better smaller than 0.3 nm/cm, so that an average background noise of about 0.2 nm/cm results.

If the tested material disks also pass this latter test, they are measured interferometrically in a third step. In contrast to the first two steps, which provide the information by measuring the polarization state of the sample and/or the light beam, which has based through the sample, the interferometry provides information regarding the transit time differences (phase differences) for the light beam, which passes through the sample. This information is acquired by a CCD chip of a digital camera, read pixel-wise and processed. The brightness values obtained grid point for grid point (pixel for pixel), or the differences in these brightness values, provide information regarding optical non-uniformities, which are derived from the above-described transit time differences. According to the current state of the art interferometers with a comparatively low spatial resolution (typically more than 1 mm pixel spacing) are always used for tests of optical components. The local structures may not be detected with sufficient accuracy with this low resolution. These measurements result in a value for the homogeneity, which is essentially determined by the good global uniformity of the crystal and, above all, by the long-range order. Next the local structures, which interfere with lithography, are determined with an interferometer with a higher spatial resolution. The spatial resolution should be selected for optimum manufacture and/or economically and technical significant. The spatial resolution should amount to at least 0.32 mm/pixel according to the magnification, preferably at least 0.2 mm/pixel, and especially at least 0.1 mm/pixel.

All the above-described measurements occur in material disks with polished surfaces, which have a minimal or small roughness. A suitable RMS roughness of the surface amounts to less than or equal to 4 nm and preferably less than or equal to 2 nm, but less than or equal to 1 nm is especially preferred.

Figure 2:
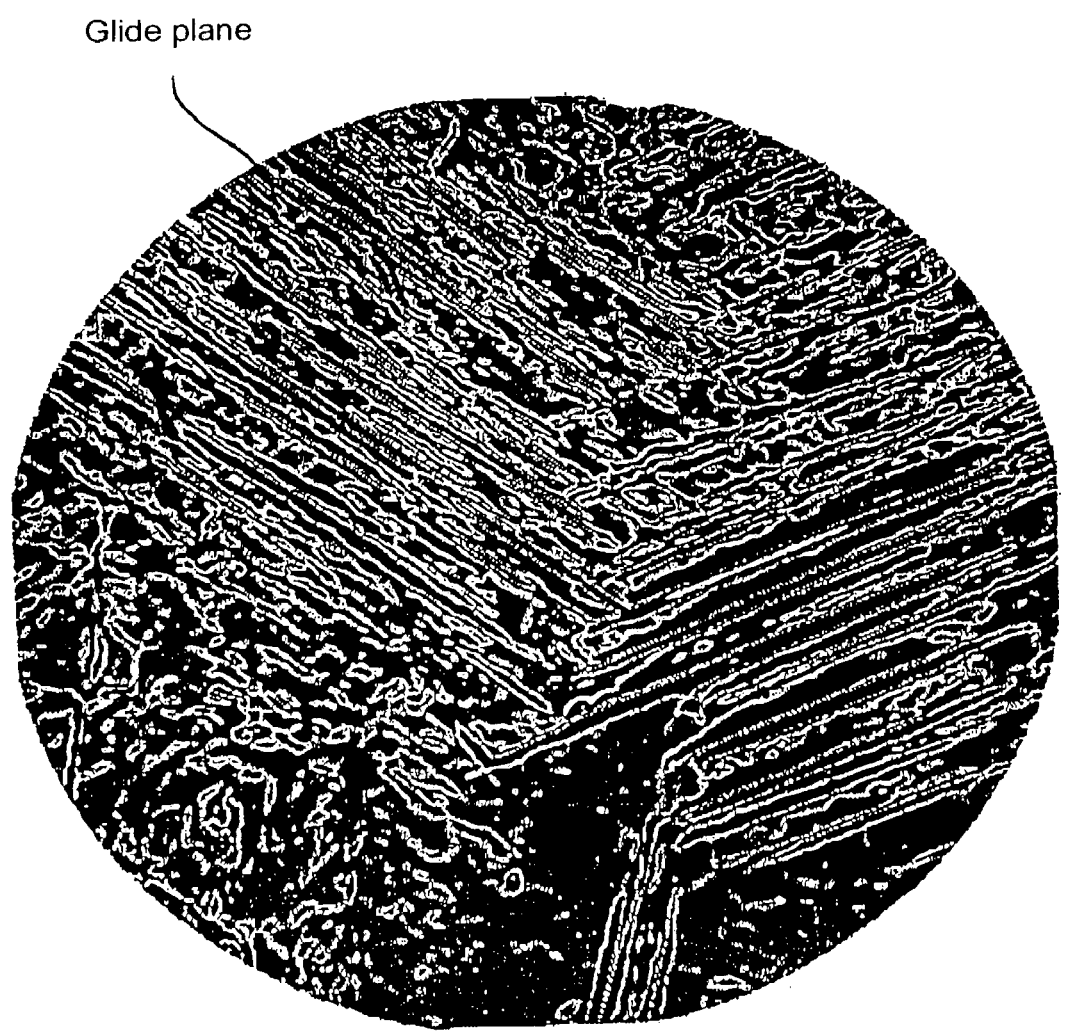
FIG. 2 is an image of a calcium fluoride crystal disk showing a number of linear glide planes.
Figure 3:
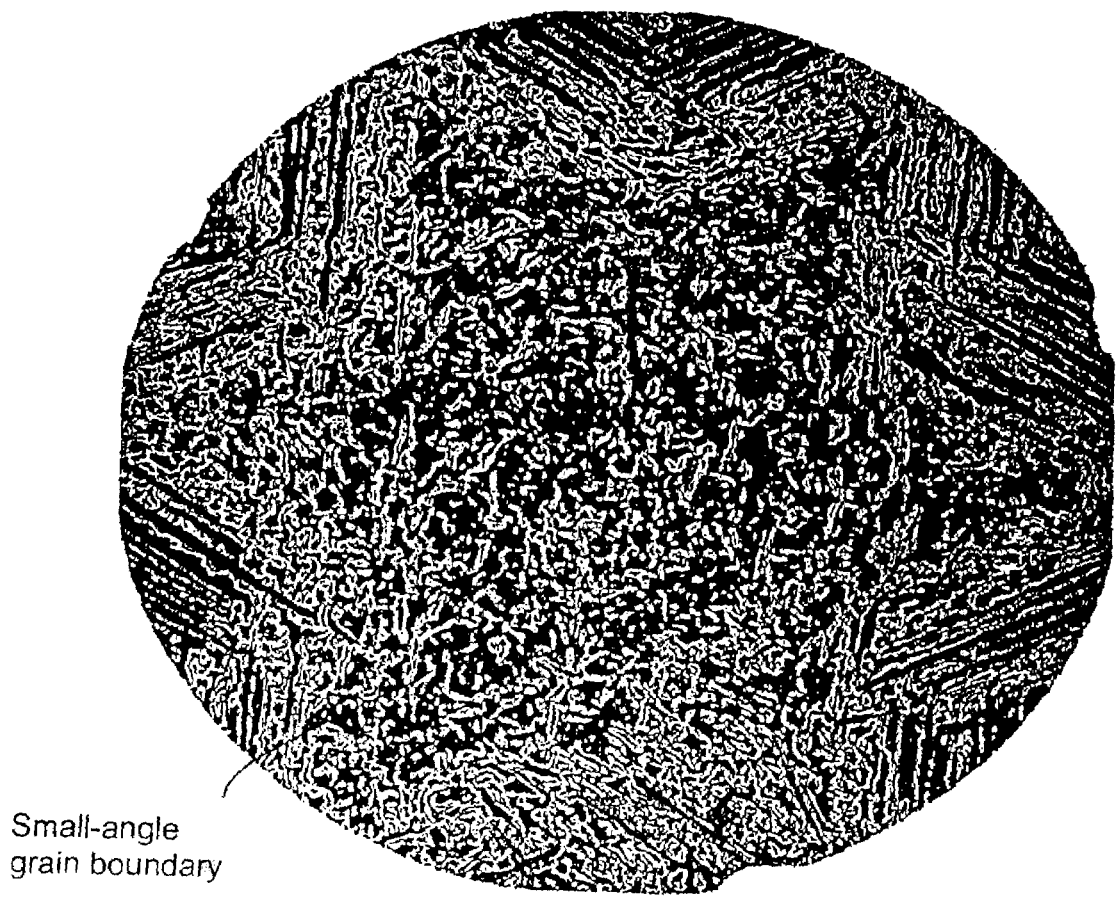
FIG. 3 is an image of a calcium fluoride crystal disk showing a number of acute angle grain boundaries.

FIGS. 2 and 3 of the drawing show, for example, images of the fine structures in a $CaF_2$ crystal disk. The image obtained with polarized monochromatic laser light (preferably HeNe 632.8 nm) shows the birefringence in the material disk. Principally other wavelengths are also usable. FIG. 2 shows a crystal disk with a number of glide planes and FIG. 3 a crystal disk with many small-angle grain boundaries. The glide planes of FIG. 2 produced by the straight band-like structures run over a large part of the crystal cross-section. FIG. 3 shows a crystal disk, which also has a few glide planes. However in the center of this crystal disk an irregular worm-like curl, which forms the small-angle grain boundaries, dominates.

The methods according to the present invention also find application in process for making various optical components, such as lenses, prisms, rectangular plates, light guide rods, optical windows and optical devices for DUV lithograph. The methods are also applicable to the manufacture of steppers and excimer lasers and thus to the making of integrated circuits and electronic devices, such as computers containing processor chips and other electronic devices, which contain chip-like integrated circuits.

The disclosure in German Patent Application DE 102 27 345.6 of Jun. 19, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method of determining local structures in optical crystals, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method for determining local structures in optical materials, especially crystals, said method comprising the steps of:
   a) observing schlieren visually in a material to be tested with divergent white light;
   b) measuring birefringence of polarized laser light in said material to be tested so as to determine local defects and structure faults in said material with a spatial resolution of at least 0.5 mm; and
   c) interferometrically measuring said material to be tested so as to determine said faults in said material to be tested by interferometry.

2. The method as defined in claim 1, wherein said spatial resolution during said measuring of said birefringence is higher than 0.2 mm.

3. The method as defined in claim 1, wherein said spatial resolution during said measuring of said birefringence is higher than 0.1 mm.

4. The method as defined in claim 1, wherein said interferometrically measuring takes place with a spatial resolution of higher than 0.2 mm.

5. The method as defined in claim 1, wherein said interferometrically measuring takes place with a spatial resolution of higher than 0.1 mm.

6. The method as defined in claim 1, further comprising polishing a surface of a disk consisting of said material to be tested to form a polished surface and performing all measurements on said disk of said material having the polished surface.

7. The method as defined in claim 1, wherein said material to be tested is a glass or a crystal.

8. The method as defined in claim 1, wherein said material to be tested is an alkali metal halide crystal, an alkaline earth metal crystal, an alkali metal oxide crystal or an alkaline earth metal oxide crystal.

9. A method for determining local structures in optical materials, especially crystals, comprises the steps of:
   a) observing schlieren visually in a material to be tested with divergent white light;
   b) only if said material is judged to be defect-free according to a predetermined standard during the observing of the schlieren visually in step a), then measuring birefringence of polarized laser light in said material to be tested so as to determine local defects and structure faults in said material with a spatial resolution of higher than 0.5 mm; and then
   c) only if said material is judged to be defect-free according to a predetermined standard during said measuring of said birefringence in step b), interferometrically measuring said material to be tested so as to determine said faults in said material to be tested by interferometry.

10. The method as defined in claim 9, wherein said material to be tested is an alkali metal halide crystal, an alkaline earth metal crystal, an alkali metal oxide crystal or an alkaline earth metal oxide crystal.

11. The method as defined in claim 9, wherein said spatial resolution during said measuring of said birefringence is higher than 0.1 mm.

12. The method as defined in claim 9, wherein said interferometrically measuring takes place with a spatial resolution of higher than 0.1 mm.

13. A method of making an optical component from a material with sufficiently small local structures, said method comprising the steps of:
   a) observing schlieren visually in a material to be tested with divergent white light;
   b) measuring birefringence of polarized laser light in said material to be tested so as to determine local defects and structure faults in said material with a spatial resolution of at least 0.5 mm;
   c) interferometrically measuring said material to be tested so as to determine said faults in said material to be tested by interferometry;
   d) judging suitability of said material to be tested on the basis of at least one of the observing of the schlieren, the measuring of the birefringence and the interferometrically measuring of said material; and then
   e) making the optical component from said material if said material is judged suitable during the judging of said material in step d).

14. The method as defined in claim 13, wherein said optical component is a lens, a prism, an optical window, an optical element for DUV lithography, a stepper, an Excimer laser, a wafer, a computer chip, an integrated circuit and an electronic device containing processor chips.

15. An optical component made by a method comprising the steps of:
   a) observing schlieren visually in a material to be tested with divergent white light;
   b) measuring birefringence of polarized laser light in said material to be tested so as to determine local defects and structure faults in said material with a spatial resolution of at least 0.5 mm;
   c) interferometrically measuring said material to be tested so as to determine said faults in said material to be tested by interferometry;
   d) judging suitability of said material to be tested on the basis of at least one of the detecting of the schlieren, the measuring of the birefringence and the interferometrically measuring of said material; and then
   e) making the optical component from said material if said material is judged suitable during the judging of said material in step d).

16. The optical component as defined in claim 15, wherein said material to be tested is an alkali metal halide crystal, an alkaline earth metal crystal, an alkali metal oxide crystal or an alkaline earth metal oxide crystal.

17. The optical component as defined in claim 15, wherein said spatial resolution during said measuring of said birefringence is higher than 0.1 mm.

18. The optical component as defined in claim 15, wherein said interferometrically measuring takes place with a spatial resolution of higher than 0.1 mm.

19. The optical component as defined in claim 15, consisting of a lens, a prism, an optical window, an optical element for DUV lithography, a stepper, an Excimer laser, a wafer, a computer chip, an integrated circuit and an electronic device containing processor chips.

* * * * *